United States Patent [19]
Frazee et al.

[11] 3,943,557
[45] Mar. 9, 1976

[54] SEMICONDUCTOR PACKAGE WITH INTEGRAL HERMETICITY DETECTOR

[75] Inventors: Lawrence E. Frazee, Huntington, N.Y.; Anthony V. Fraioli, Essex Fells, N.J.

[73] Assignee: Plessey Incorporated, Melville, N.Y.

[22] Filed: Oct. 31, 1974

[21] Appl. No.: 519,605

Related U.S. Application Data

[62] Division of Ser. No. 443,436, Feb. 19, 1974, Pat. No. 3,890,703.

[52] U.S. Cl. ............... 357/75; 174/52 S; 324/65 R; 338/35; 357/26
[51] Int. Cl.² ......................................... H01L 23/16
[58] Field of Search .............. 357/26, 75; 174/52 S; 324/65 R; 338/35

[56] References Cited
UNITED STATES PATENTS

| | | |
|---|---|---|
| 3,404,215 | 10/1968 | Burks et al. ............................ 357/75 |
| 3,471,753 | 10/1969 | Burks et al. ............................ 357/75 |
| 3,479,572 | 11/1969 | Pokorny ................................. 357/26 |
| 3,497,774 | 2/1970 | Hornberger et al. ................. 357/75 |
| 3,600,650 | 8/1971 | Obenhaus .............................. 357/75 |
| 3,657,805 | 4/1972 | Johnson ................................ 357/75 |
| 3,820,152 | 6/1974 | Booth ................................... 357/75 |

*Primary Examiner*—Andrew J. James
*Attorney, Agent, or Firm*—James J. Burke II

[57] ABSTRACT

The operation of relative humidity sensors made from cobalt oxide on a non-conductive ceramic substrate is improved by heating the sensor for a short period to a high temperature in a reducing atmosphere. This reduces the specific resistance of the device. With a lower resistivity, it is possible to reduce the size of the sensor to the point where it can be included along with a semiconductive device in standard hermetic packages. This makes possible the continuous, one-line monitoring of hermeticity for the life of the circuit without the necessity fo applying a load to the circuit.

4 Claims, 4 Drawing Figures

SEMICONDUCTOR PACKAGE WITH INTEGRAL HERMETICITY DETECTOR

This is a division of application Ser. No. 443,436, filed Feb. 19, 1974, now U.S. Pat. No. 3,890,703 issued June 24, 1975.

BACKGROUND OF THE INVENTION

The present invention relates in general to relative humidity sensors and, more particularly, the invention relates to sensors made from cobalt oxide as the active element. Humidity sensors of this type are also referred to as hygrometers or humistors, as it is their electrical resistivity which changes with humidity.

Procedures for manufacturing cobalt oxide humidity sensors or hygrometers are well known. The starting material is a cobalt oxide powder. As pure CoO powder is very expensive, the starting material is generally a mixture of CoO with some $Co_3O_4$, but the latter compound dissociates at about 900°C. so the completed sensor will be essentially CoO, the cobaltous oxide. This compound is stable up to its melting point, which is above 1800°C.

The finely divided powder, preferably minus 325 mesh, is mixed with an inert liquid vehicle and viscosifiers to form a screen-printable paste. A thin layer of the paste is then screen-printed in a desired pattern onto a dielectric, high-temperature resistant substrate, typically a high-alumina ceramic. The screened pattern is then dried and fired in air at a temperature in the range of 1350°C. to 1550°C. Electrodes can be preformed on the substrate, co-fired with the paste, or applied in a subsequent operation. The latter is the more common approach as it is generally desired to have the electrodes in a rather elaborate, interdigitated pattern on the top surface. Conductive inks or pastes (platinum-gold, palladium-gold, etc.) are used in the conventional manner.

Before such a sensor can be put to use, it must be accurately calibrated to determine the change in electrical resistance with relative humidity.

The very high specific resistivity of cobalt oxide, which is $10^6$ ohms per square or higher, requires that humidity sensors made therefrom be relatively large in order to produce a suitable output. Typically, prior art humidity sensors of this type are manufactured on one inch square substrates. This is of course much too large to be included in integrated circuit packages.

The desirability of having a humidity sensor within a hermetically sealed semiconductor package is manifest. Essentially all semiconductive devices are humidity-sensitive to a greater or lesser degree. As a result, specifications on hermeticity for packages are most stringent. But, while technology for producing hermetic packages is well developed and tests therefor standarized, the fact that a package is hermetic initially says nothing about whether it will remain so after months or years of service, often under severe conditions of shock and vibration. Further, the failure of a seal in service can now be detected only by a malfunction or failure of the circuit.

PRIOR ART

The production of cobalt oxide hygrometers is disclosed by Delaney et al. in U.S. Pat. No. 3,345,596. The two patents of Nicholas, U.S. Pat. Nos. 3,703,697 and 3,715,702, disclose the use of humectants to increase water absorption on hygrometer surfaces of this same type. In one instance the oxide is converted in part to the oxychloride, and in the other, a coating of lithium chloride or polyethylene glycol is provided. Blythe et al. U.S. Pat. No. 3,105,214, disclose the use of a vapor-permeable ion-selective membrane on the sensor surface. This will swell up in a humid environment and transport water but no ions to the sensor surface.

OBJECT OF THE INVENTION

A general object of the present invention is to provide improved humidity sensors of the cobalt oxide type.

Another object of the present invention is to provide a cobalt oxide humidity sensor which is smaller than prior art sensors.

A further object of the present invention is to provide a cobalt oxide humidity sensor within a hermetically sealed semiconductor package.

A still further object of the present invention is to provide a cobalt oxide humidity sensor having a lower resistivity than prior art sensors of the same general type.

Yet another object of the present invention is to provide a cobalt oxide humidity sensor very sensitive in the low-ppm range.

A still further object of the present invention is to provide a semiconductor package with a built-in or integral humidity sensor.

Various other objects and advantages of the invention will become clear from the following description of embodiments thereof, and the novel features will be particularly pointed out in connection with the appended claims.

THE DRAWINGS

Reference will hereinafter be made to the accompanying drawings wherein.

DESCRIPTION OF EMBODIMENTS

Figure 1:
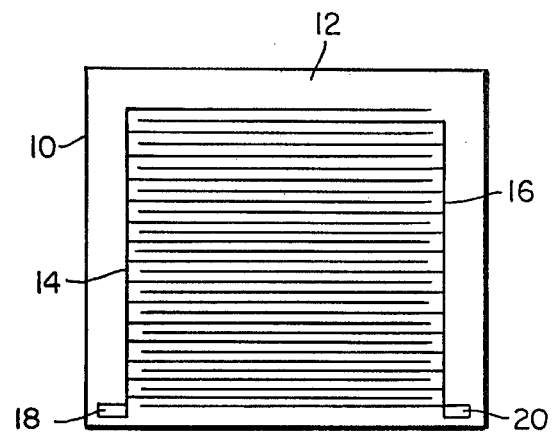
FIG. 1 is a plan view of a typical humidity sensor.

The present invention comprises, in essence, lowering the specific-resistivity of the cobalt oxide film by heating the previously fired film to a high temperature in a reducing atmosphere for a brief period. The atmosphere is preferably hydrogen. This treatment has been observed to reduce the resistivity of the film by 1 to 1.25 orders of magnitude. Thus, an air-fired CoO film with a resistivity of $3.76 \times 10^6$ ohms/square has a resistivity of $6.3 \times 10^4$ ohms per square after firing in hydrogen at 1500°C. for 15 minutes.

The reasons why this treatment reduces resistivity are unclear, just as the mechanism of conduction in cobalt oxide is unclear. It is possible that the reducing gas attacks the CoO crystalline boundaries preferentially and exposes more surface with a higher surface energy. It is not known whether CoO conducts with surface electrons or "holes" in the bulk material; it is felt to be possible that the hydrogen firing could contribute to bulk conductivity because of the higher surface energy conditions.

It is believed that the prior-art (Delaney et al.) teaching of firing the cobalt oxide for a brief period only and at a high temperature (1500°C.) is designed to provide a large number of very small CoO crystals and prevent crystal growth. The hydrogen treatment of the present invention may significantly increase the population-density of exposed crystal edges and corners. Because of the interrupted lattice periodicity at these locations, and resultant dangling or broken bonds, these sites should be preferred locations for gas adsorption-desorption phenomena involved in the relative humidity equilibration process.

The hydrogen firing process has been optically observed to produce etch pits on the CoO surface which are quasi-hexagonal in plane view and conical in cross-section, with terraced walls. Etch lines about larger, pyramidal-shaped crystals parallel to a base plane have also been observed. It is believed that such exposed crystal surfaces should enhance gas-surface interaction phenomena.

The lowering of the CoO resistivity is desirable for several reasons, the most important of which is that it permits a substantial reduction in the size of the humistor. Thus, heretofore a typical humistor had to be mounted on a 1 inch square substrate, to allow for device and conductive geometry that would give a suitable output. In accordance with the present invention, humistors of the same resistance are produced on 0.20 by 0.20 by 0.040 inch substrates with the same (1–5 volt) outputs and improved linearity of response.

This permits humsitors of the present invention to be used for the first time as hermeticity detectors within semiconductive device packages. As noted hereinabove, stringent hermeticity requirements are imposed in both military and commercial electronics specifications, because humidity has a disastrous effect on the operation of both active and passive microcircuit elements. Heretofore, it has not been possible to detect hermeticity failures, i.e. leaks, except through circuit mal-functions. With the miniaturized humidity sensors produced in accordance with the present invention, it becomes possible to include the device on the substrate within the can or package. In operation with a nominal bias, it will be essentially non-conductive. If the package fails and even a few ppm of moisture are encountered, the sensor will be rendered sufficiently conductive to trigger an alarm. Thus, with the present invention it is possible to continuously monitor hermeticity without waiting for circuit damage, mal-function or failure, and hermeticity monitoring is carried out without loading the main circuit. More particularly, humistors of the present invention may have a total wet-to-dry resistance change of as much as six or seven orders of magnitude. This very great change is believed to account for the substantial sensitivity in the very low ppm (high resistivity) range.

Humistors made in accordance with the present invention resemble prior art devices except insofar as the hydrogen firing tends to change the normally rather glossy CoO surface to a more matte-like appearance. As shown in FIG. 1, a ceramic substrate 10 has a layer of cobalt oxide 12 screened and fired over its entire surface (or less than the entire surface, as desired). First and second electrode patterns 14, 16 which terminate in bonding pads 18, 20 are then screened and fired. After firing in a reducing atmosphere (which may occur before or after application of electrodes) the device is complete.

Figure 2:
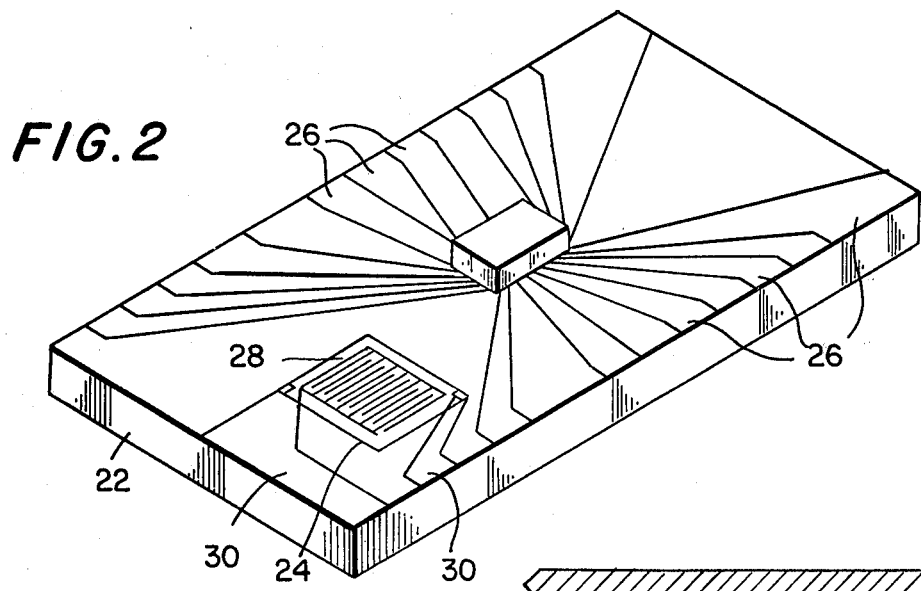
FIG. 2 is a perspective view of a portion of an integrated circuit package including an integral humidity sensor in accordance with this invention.

FIG. 2 illustrates a humidity sensor of the present invention incorporated into a standard dual in-line 14-lead package. The substrate 22 first has a cobalt oxide area 24 screened and fired thereon. Thereafter, the integrated circuit leads 26, the humistor electrodes 28, and leads therefore 30 are all screened and fired simultaneously. The entire unit is then fired in hydrogen, since this will not effect the metallic patterns. Installation of the integrated circuit 32 or other semiconductive device, sealing and testing follow conventional procedures, except that further exposure to reducing atmospheres should be avoided.

Figure 4:
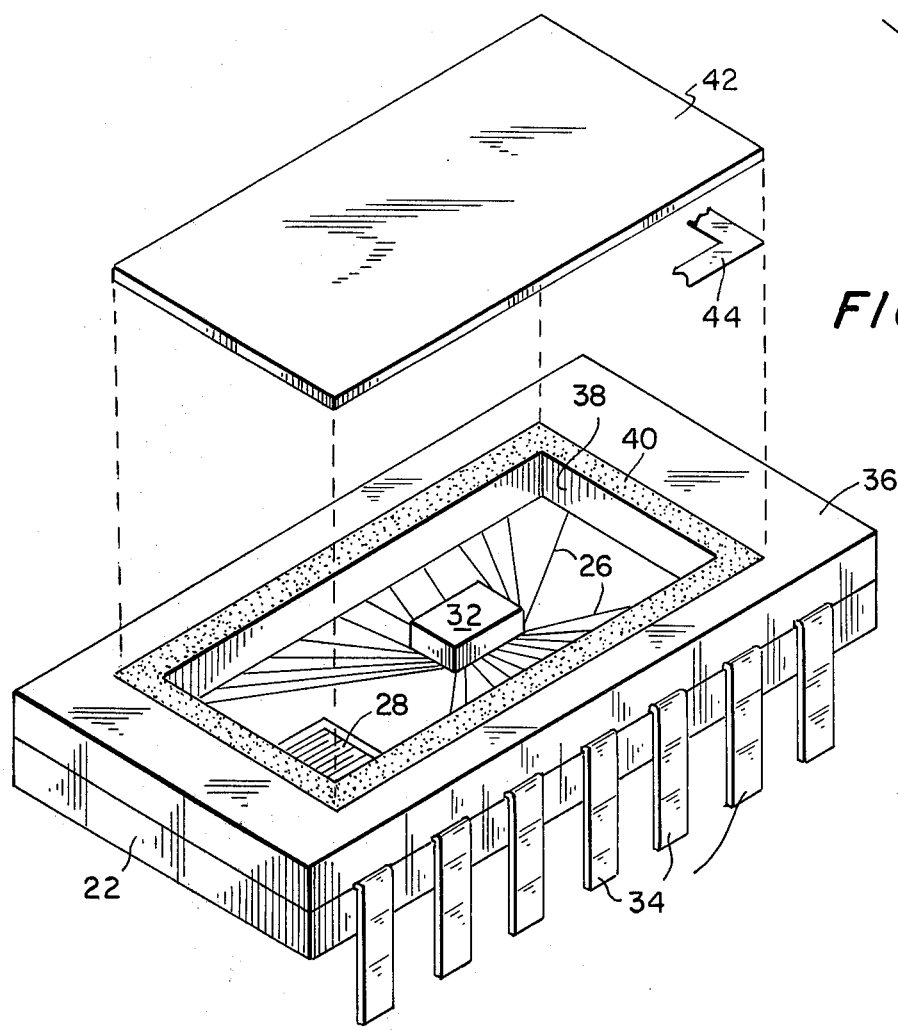
FIG. 4 is a perspective view of the FIG. 2 package assembled and ready for sealing.

FIG. 4 illustrates the package of FIG. 2 when ready for hermetic sealing. A lead frame including leads 34 has been brazed to the leads 26 on the substrate, and a ceramic spacer 36 having an opening 38 forming a cavity is bonded thereover (those skilled in the art will appreciate that these steps are part of package manufacture and are normally carried out prior to insertion and bonding of circuit 32). The top surface of spacer 36 includes a metallized and plated ring 40 around opening 38 to facilitate hermetic sealing. The latter is accomplished with a lid 42 having a mirror image of ring 40 on its bottom surface (not shown) and a brazing preform 44, of gold-tin, Foballoy (trademark) or other brazing alloy. Except for the presence of sensor 28 in the cavity, these steps are entirely conventional.

Understanding of the invention will be facilitated by reference to the following specific example, which is to be construed as illustrative only and not in a limiting sense.

EXAMPLE

Figure 3:
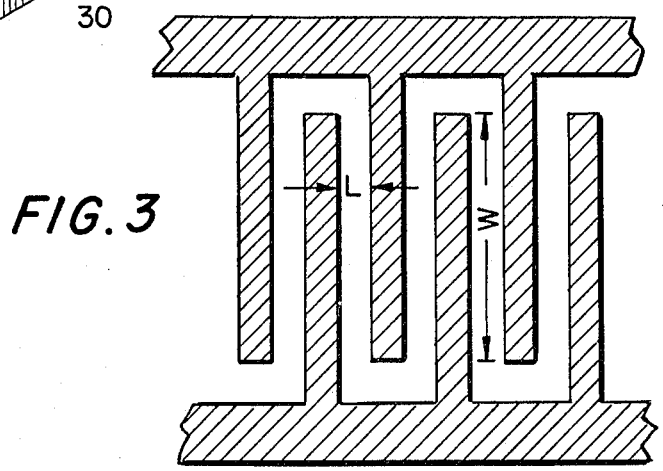
FIG. 3 is an enlarged view of a portion of the sensor of FIG. 1, illustrating resistivity calculations.

In humistors (or resistors) of the general type described, calculation of resistivity in ohms/squre is more complex than for simple thick film geometries, and depends on the space between respective interdigitated electrodes and their length. With reference to FIG. 3, the number of squares is calculated according to the following formula:

$$\text{No. of squares} = \frac{L}{W} \times \frac{1}{(N-1)} \qquad (1)$$

In Equation 1, N is the total number of conductor lines, so N-1 is the number of resistor lines. The factor L/W is multiplied by the reciprocal of N-1 because, while L is constant throughout the pattern, W is lengthened by each pair of conductors, and it is this which must be multiplied by N-1. As will be apparent from the data hereinbelow, this produces resistors with very small numbers of squares.

Cobalt oxide paste was screened and fired onto one inch substrates in a 950 mil square pattern and fired. One group of substrates was fired in hydrogen and all substrates had identical conductives applied, wherein $L = 15$ $W = 800$ $N = 26$ (all dimension being in mils).

In accordance with equation 1, the number of squares was $7.5 \times 10^{-4}$. At 100% relative humidity, the resistors that were not hydrogen fired had resistances of 3.2 ×

$10^6\Omega$ and those that were so treated measured $1.9 \times 10^5\Omega$. In terms of ohms/square, these figures convert to $4.26 \times 10^9$ and $2.53 \times 10^8$, respectively.

The same paste was screened in 200 mil square patterns and, again one group was fired in hydrogen and another was not. Conductives were applied in a pattern where $L = 15$ $W = 180$ $N = 8$ The number of squares in this pattern is $1.19047 \times 10^{-2}$. During processing, film thickness, firing parameters etc. were all closely controlled so that the films were comparable except for size and conductive geometry. On these units, at 100% R.H., resistance of the non-hydrogen fired units was $5.07 \times 10^7\Omega$ and those that were so treated measured $3.01 \times 10^6\Omega$. Resistance of 200 mil square humistors treated in accordance with the present invention is thus seen to be substantially the same as 950 mil square units that were not so treated (i.e. $3.2 \times 10^6\Omega$).

Humistors are calibrated by plotting log R vs. relative humidity over the entire humidity range. A problem with known humistors has been an asymptotic resistance change (or other anomalies) as R.H. approaches 0%. An advantage of humistors made in accordance with the present invention is a substantially linear response over the entire R.H. range. This greatly simplifies required circuitry and makes the devices useful as hermeticity detectors, where R.H. must be measured in parts-per-million. The reason why the reducing-gas treatment brings about this desirable improvement is not understood.

It will be appreciated by those skilled in the art that FIG. 2 is illustrative only and is not to be construed in a limiting sense, since many variations are possible. Thus, a discrete humistor as shown in FIG. 1 could be incoporated into a semiconductor package rather than having the package manufactured with an integral device. The humistor could be wired into the main circuit if that condition could be tolerated. Different package designs offer varying opportunities for placement of the sensor. In packages having glass-sealed ceramic lids for example, it would be possible to have the sensor printed on the under-side of the lid. Discrete or integral sensors could be incorporated into header cans. In laminated packages having leads on a raised step section surrounding the device in a central cavity, the sensor could be placed on either level.

It will be further appreciated that the small size of humistors of the present invention permits their incorporatin in a variety of other devices where hermeticity is important. Image intensifier tubes or other electronic tubes are one example. Optical systems where hermeticity is required to avoid condensation on optical elements is another example.

Various other changes in the details, steps, materials and arrangements of parts, which have been herein described and illustrated in order to explain the nature of the invention, may be made by those skilled in the art within the principle and scope of the invention as defined in the appended claims.

What is claimed is:

1. A hermetically-sealable package for a semiconductive device including an integral hermeticity detector comprising:

means forming a cavity adapted to retain said semiconductive device and including a dielectric substrate;

a plurality of metallic leads extending from within said cavity to the outside of said package;

a humidity sensor within said cavity, said sensor comprising a double-fired layer of cobalt oxide, said layer having a lower than normal resistivity as a result of a second firing in a reducing atmosphere at about 1500°C. for a brief period;

a pair of electrodes on said double-fired layer connected to a pair of said leads; and seal means for hermetically sealing said cavity.

2. The package as claimed in claim 1, wherein said sensor is a discrete element formed on a high-temperature resistant, dielectric substrate.

3. The package as claimed in claim 1, wherein said sensor is formed on said dielectric substrate.

4. The package as claimed in claim 1, wherein said sensor is formed on said seal means.

* * * * *